United States Patent
Keenan et al.

(10) Patent No.: US 7,348,299 B2
(45) Date of Patent: *Mar. 25, 2008

(54) CLEANSING BAR WITH DISTRIBUTED POLYMERIC NETWORK PROVIDING ENHANCED DELIVERY

(75) Inventors: Diane Marie Keenan, Derby, CT (US); Andre Marie Puleo, Stratford, CT (US); Melissa Ann Cline, East Hartford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/152,600

(22) Filed: Jun. 14, 2005

(65) Prior Publication Data

US 2006/0281650 A1 Dec. 14, 2006

(51) Int. Cl.
*A61K 7/50* (2006.01)
(52) U.S. Cl. .................. 510/141; 510/144; 510/146; 510/155
(58) Field of Classification Search .................. None
See application file for complete search history.

(56) References Cited

U.S. PATENT DOCUMENTS

| | | |
|---|---|---|
| 3,949,137 A | 4/1976 | Akrongold et al. |
| 4,190,550 A | 2/1980 | Campbell |
| 4,613,446 A | 9/1986 | Magyar |
| 4,969,225 A * | 11/1990 | Schubert .................. 15/229.12 |
| 5,221,506 A | 6/1993 | Dulin |
| 6,171,007 B1 | 1/2001 | Hsu |
| 6,190,079 B1 | 2/2001 | Ruff |
| 6,673,756 B2 * | 1/2004 | Sonnenberg et al. ........ 510/141 |
| 6,893,182 B1 | 5/2005 | Liao |
| 6,896,435 B1 | 5/2005 | Rink |
| 2003/0220212 A1 | 11/2003 | DeVitis |
| 2004/0033915 A1* | 2/2004 | Aleles et al. ................ 510/141 |
| 2005/0112370 A1 | 5/2005 | Stockman et al. |
| 2005/0276828 A1* | 12/2005 | Grissett et al. ............. 424/401 |
| 2005/0277566 A1 | 12/2005 | Grissett et al. |
| 2005/0277567 A1* | 12/2005 | Macedo et al. ............. 510/438 |
| 2005/0277568 A1 | 12/2005 | Keenan et al. |
| 2007/0049512 A1 | 3/2007 | Keenan et al. |

FOREIGN PATENT DOCUMENTS

EP 1 266 599 A1 12/2002

\* cited by examiner

*Primary Examiner*—Necholus Ogden
(74) *Attorney, Agent, or Firm*—Michael P. Aronson

(57) ABSTRACT

An article especially suitable for cleansing skin having the general form of a fibrous cleansing bar is described which includes a hydrous lathering composition that at least partially incorporates a fabricated polymer network that is exposed either before or during use. The fibrous cleansing bar exhibits an enhanced release of hydrophobic organic benefit agents used to deliver sensory, skin care or other functional benefits.

12 Claims, No Drawings

CLEANSING BAR WITH DISTRIBUTED POLYMERIC NETWORK PROVIDING ENHANCED DELIVERY

FIELD OF INVENTION

The invention relates to cleaning articles having the form of a fibrous bar wherein a solid or semi-solid hydrous lathering composition at least partially incorporates a fabricated polymeric network. The cleansing articles exhibit an enhanced release of hydrophobic organic benefit agents especially perfumes.

BACKGROUND OF INVENTION

Consumers have been increasingly receptive to new personal washing systems that provide better skin care, greater refreshment or that have generally led to a more pleasurable bathing and showering experience. Although toilet bars are still widely used because of their convenient form and simplicity, liquid products and more recently sheets have grown in popularity.

Consumers recognize that liquids provide excellent skin care and fragrance attributes. However, this product form does not lather well without the use of an additional implement and without such an implement, liquids are not perceived as economical. Sheets in contrast, lather well but are generally single-usage forms and thus are primarily used in facial washing where the perceived benefits more readily justifies their higher cost.

Liquid and sheet personal washing forms have primarily been targeted to female consumers, and these forms are not so widely used by men who often prefer bars for their convenience and refreshment qualities.

Thus, there is a need for cleansing articles that have the convenience and economy of a bar but that deliver the sensory and skin care benefits of a liquid.

The following patents and publications form a part of the related art.

U.S. Pat. No. 4,613,446 describes plastic mesh pads and sponges impregnated with a soft paste-like cleansing composition including an alkali metal phosphate, a wetting agent, fatty acid soap, a chelating agent and surfactant. The articles are designed to be used as large size scouring pieces for cleaning tires, vinyl tops and trims, bumpers and other surfaces.

U.S. Pat. No. 3,949,137 describes a gel-impregnated sponge composed of two layers: one layer is impregnated with a hardened gel material and one layer is an unimpregnated sponge.

U.S. Pat. No. 5,221,506 describes a bar soap having a sponge core which is revealed after the soap bar is reduced to a sliver, said sponge core providing support and preventing breakage of the sliver thus reducing wastage.

U.S. Pat Application Publication No. 2003/0220212 A1 describes bar soap reinforced with a reinforcement member such as a mesh to prolong the usage of the bar.

U.S. Pat. No. 6,190,079 describes a scrubbing soap bar composed of vegetable oil and glycerin into which is partially imbedded a thin fine-mesh netting that serves as a feature to facilitate grasping and holding the bar.

U.S. Pat. No. 4,969,225 relates to a bathing and cleansing article in the form a scrub brush specifically made to contain or hold a bar of soap.

U.S. Pat. No. 4,190,550 describes a seamless fibrous, soap-filled pad in the form of an envelope that surrounds a solid soap, which is held in integral form by the entanglement of the fibers.

U.S. Pat Application Publication No. 2004/0033915 A1 relates to cleansing bars including a cleansing composition and a plurality of discrete elements (e.g., fibers) having a length to diameter ratio of from about 50 to 1 to about 100,000 to 1.

EP 1 266 599 A1 describes a solid cleanser holder composed of an apertured textured film surrounding a solid cleanser. The film reduces slip, exfoliates and enhances lather.

U.S. Patent Application Publication No. 2005/0113270 A1 to Stockman et al published May 26, 2005 relates to scrubbing soap bar having an embedded scrubbing element.

U.S. Pat. No. 6,6896,435 to James W. Rink issued May 24, 2005, describes a slip-resistant floating soap having two outer convex shaped layers of soap connected by a water impermeable buoyant material extending around the outer soap layers to provide slip resistance.

U.S. Pat. No. 6,893,182 to Chung Min Liao issued May 17, 2005 describes a soap device having an embedded spongy or perforated cleansing device.

The present invention seeks improvements over deficiencies in the known art. Among the one or more problems addressed include the development of a personal cleansing article having a higher delivery of fragrance, and other hydrophobic benefit agents, that is convenient and economical to use.

SUMMARY OF THE INVENTION

The inventors have developed a cleansing article that provides the desirable benefits of a liquid, e.g., fragrance impact, and skin care with the convenience and economy of the bar form. The article includes a hydrous composition within which is at least partially distributed a fabricated polymeric network. The inventive fibrous cleansing bar surprisingly provides a greater release and deposition of water insoluble insoluble or sparingly water soluble (hydrophobic) "benefit agents" such as perfumes than conventional personal washing bars.

The article can be manufactured in a variety of shapes including those of a traditional personal washing bar and thus are appealing to male consumers. The combination of the different sensory stimuli that are provided by the distributed polymer network has been found to be highly appealing to many consumers.

These and other advantages of the compositions disclosed herein will become clear from the description of the invention.

More specifically, the invention is a fibrous cleansing bar that includes:
  i) a fabricated polymer network; and
  ii) a solid or semisolid hydrous lathering composition in which is at least partially distributed the fabricated polymer network, said hydrous lathering composition comprising:
    a) a foaming surfactant;
    b) an organic benefit agent having an octanol/water partition coefficient of at least about 500;
    c) water;
    d) optionally, a water soluble organic solvent;
      wherein the water plus the optional water soluble organic solvent comprises at least about 40%, preferably at least 45% and most preferably at least 50% of the hydrous solid or semi-solid lathering composition by weight;

wherein the fabricated polymer network is distributed throughout at least about 55% of the volume of the hydrous lathering composition, preferably at least 80% of the volume and most preferably at least about 90% of the volume of the hydrous lathering composition; and wherein the weight ratio of the hydrous lathering composition to the fabricated polymer network is in the range from about 30 to 1 to about 2000 to 1.

In one embodiment, the hydrophobic organic benefit agent includes either or both Type 2 and Type 3 perfume molecules. Type-2 perfume molecules is defined as perfume molecules having an octanol/water partition coefficient of at least 500 and a volatility constant of less than about 20 atmospheres (Atm—in SI units 1 Atm=$1.0132 \times 10^5$ Pascals (Pa)). Type-3 perfume molecules is defined as perfume molecules having an octanol/water partition coefficient of at least 500 and a volatility constant of at least about 20 Atm.

In another embodiment the fabricated polymer network is a continuous network of either bonded or partially entangled fibers.

In still another embodiment, the fabricated polymer network is a reticulated open cell foam.

DETAILED DESCRIPTION OF THE INVENTION

As used herein % or wt % refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

For the avoidance of doubt the word "comprising" is intended to mean "including" but not necessarily "consisting of" or "composed of." In other words, the listed steps or options need not be exhaustive.

The subject invention provides an article for personal cleansing having the general aspect or form of a bar that includes an hydrous lathering within which is at least partially distributed a fabricated polymeric network.

The fabricated polymer network, the hydrous lathering composition and methods to prepare and evaluate the inventive article are described in detail below.

Fabricated Polymer Network

The inventive article includes a fabricated polymer network (hereinafter alternatively designated "FPN") at least partially distributed in a hydrous solid or semi-solid lathering composition (hereinafter alternatively designated "hydrous composition") as described below. By the term partially distributed is meant that the fabricated polymer network should occupy at least 55%, preferably at least 75% and most preferably at least about 90% of the volume of the hydrous composition.

It should be understood that the fabricated polymer network is a porous network, preferably a highly porous network, comprised of a minor volume fraction of solid polymer and a major volume fraction of "void space". This void space is occupied by the medium in which the FPN is immersed. Consequently, although the FPN occupies most of the geometric volume of the hydrous composition as well as the fibrous bar, it generally makes up only a small fraction on a weight basis: about 0.05% to about 3% by weight of the fibrous bar.

By a "fabricated polymeric network", is meant that the network is synthetic or man-made, and that this network is predominantly composed of a polymeric material. Thus, animal of vegetable sponges which are hard and scratchy when dry and require water for plasticization are outside the scope of the invention. However, the polymer making up the fabricated network can be synthetic (e.g., polyethylene), naturally occurring (e.g., cellulose) or a hybrid (e.g., cotton/polyester).

Fabricated polymer networks suitable for the invention must first and foremost be suitable for frequent use as a cleansing implement in showering and bathing: they should not be scratchy or highly abrasive. Thus, soft diamond-mesh sponges of the type described in U.S. Pat. No. 5,144,744 to Campagnoli and commonly known as a pouf or a puff and related networks can be employed.

One suitable and preferred FPN is 3-dimensional non-woven material also called a "batting layer", having a length (i.e. the major axis) and width (i.e. the minor axis) oriented in the x-y plane and a height oriented along its z axis. Non-woven FPN useful for the present invention can range in basis weight from about 25 $g/m^2$ to 1000 $g/m^2$ The non-woven FPN contains a large number of fiber-to-fiber bonds. Such continuous networks of bonded fibers are achieved by using one or a combination of chemical or thermal bonding. The batting layer may advantageously have from about 0.25 to about 7 or more fiber to fiber bonds per cubic millimeter. Preferably, the batting layer has about 0.5 to 5 fiber to fiber bonds per cubic millimeter and most preferably has a minimum of about 1 to 3 fiber to fiber bonds per cubic millimeter. Such fiber bonds may be quantified using art recognized or equivalent techniques such as the method described below.

Suitable non-wovens are comprised of synthetic and/or natural fibers converted into continuous networks by conventional, well-known non-woven, woven or knit processing systems or combinations thereof. Generally well known non-woven processing systems transform fibers and filaments directly into useful cohesive structures with adequate strength that are not manufactured via knitting or weaving. Useful synthetic fibers include but are not limited to polyethylene, polypropylene, polyester, low-melt polyester, viscose rayon, polylactic acid and polyamide and blends/combinations thereof and the like. Further examples of synthetic materials useful as components in the present invention include those selected from acetate fibers, acrylic fibers, cellulose ester fibers, and methacrylic fibers. Examples of some of these synthetic materials include acrylics such as Acrilan®, Creslan®), and the acrylonitrile-based fiber, Orion®; cellulose ester fibers such as cellulose acetate, Arnel®, and Acele®; polyamides such as Nylons (e.g., Nylon 6, Nylon 66, Nylon 610 and the like); polyesters such as Fortrel®, Kodel®, and the polyethylene terephthalate fibers, Dacron®.

Additionally synthetic fibers used herein can be described as staple and continuous filaments including any blend thereof. Non-limiting examples of natural materials useful in the fibrous assembly in the present invention are silk fibers, keratin fibers and cellulosic fibers. Non-limiting examples of keratin fibers include those selected from wool fibers, camel hair fibers, and the like. Non-limiting examples of cellulosic fibers include those selected from wood pulp fibers, cotton fibers, hemp fibers, jute fibers, flax fibers, viscose fibers (rayon) and mixtures thereof. Additionally fibers used herein may include multi-component fibers or combinations thereof. Useful fiber deniers included herein range from about 1 denier to 20 denier including any combinations within this range.

With respect to manufacturing methods for non-wovens useful in the present invention, fibers are separated, oriented and deposited on a forming or conveying surface. Methods used to arrange or manipulate fibers described herein into a fibrous assembly include but are not limited to carding/garnetting, airlay, wetlay, spunbond, meltblown, vertical lapping or any combination/iteration thereof and the like. Cohesion, strength and stability may be imparted into the fibrous assembly via a bonding mechanism that include but are not limited to needlepunching, stitch bonding, hydroentangling, chemical bonding and thermal bonding and any combination/iteration thereof and the like. Fibers that comprise a fibrous structure/assembly may also be used that are not chemically, and thermally bonded to one another to supplement the continuous bonded network of the inventive bar. Such structures that form a plurality of fiber to fiber contacts are all well suited for the present invention.

Some preferred embodiments of useful non-woven FPN include vertical lapped non-wovens, which can be further described as having a given number of pleats per linear unit, i.e., pleats per cm. In this regards, pleats per cm is defined as the number of folds present in a cm of non-woven. This can be measured by placing two marks a fixed distance apart, e.g., 2.54 cm in the machine direction of the non-woven. Subsequently, a count of the number of folds between the two marks is taken. The resultant count divided by the length between markings is taken as pleats per cm. A suitable high bulk corrugated non-woven fabrics are described in U.S. Pat. No. 3,668,054 to Stumpf issued on Jun. 6, 1972; and U.S. Pat. No. 4,576,853 to Vaughn et al. Issued on Mar. 18, 1986; which are incorporated in their entirety by reference herein.

There are a variety of other ways that pleats can be arranged within the FPN to enhance its resiliency and usefulness as illustrated below.

In one arrangement, the non-woven network is a corrugated bulky fabric that has pleats oriented substantially perpendicularly to the x-y plane of the fibrous bar. The x-y plane is defined as the plane of largest surface of the article, i.e., the surface that mainly comes in contact with the skin during cleansing. Preferably there should be about 2.5 pleats per cm to about 15 pleats per cm, i.e., about 1 to 6 pleats per inch. Generally, the pleats will adhere together either through the use of an adhesive or by entanglements.

In another arrangement the non-woven network is a corrugated bulky fabric that has a plurality of discrete peaks. The peaks form a 3 dimensional pattern where the major axis of the peaks is substantially aligned with the z axis of the fabric, i.e., the axis that is oriented substantially perpendicularly to the x-y plane of the fibrous bar. Preferably the number of peaks per square cm is in the range of about 0.25 to about 3 peaks per square cm. Again adhesive or entanglement is generally used to reinforce the corrugated structure.

In another corrugated arrangement, the bulky fabric has a polygonal regular or irregular 3 dimensional honeycomb-like structure of approximately cylindrical cells. Here the major axis of each cylindrical cell of the honeycomb-like structure is oriented substantially perpendicularly to the x-y plane of the fibrous bar.

In yet another corrugated variant, the bulky fabric has a plurality of attached layers oriented substantially perpendicularly to the x-y plane of the cleansing article. Here, the attached layers can be arranged in an arbitrary pattern composed of one or more of spiral, wavy or folded arrangement(s).

A second type of fabricated polymer network is composed of individual cut or chopped fibers that form a non-bonded mat or web in which the fibers are not chemically of physically bonded but can be an entangled mass. In this embodiment the fibers have a length to diameter ratio of from about 50 to 1 to about 100,000 to 1.

The non-bonded fibers may be made from a wide range of materials, both natural and synthetic, so long they have a length to diameter ratio of from about 50 to 1 to about 100,000. The length of the non-bonded fibers generally varies from about 0.125 to about 5.0 inches, e.g., about 1 to about 2 inches.

The denier of the non-woven fibers may vary depending on the benefit desired. Typically, the denier ranges from about 0.025 to about 25, more preferably from about 1.5 to about 15, and most preferred from about 3 to about 9.

Suitable fibers include but are not limited to monofilament and multifilament fibers, monocomponent and/or multicomponent and mixtures thereof. Preferred are fibers of polyester; polyolefins, such as polyethylene and polypropylene; polyamide; rayon; cotton; hemp; wool; and combinations thereof. Examples of suitable polyamide fibers include Nylons, such as, NYLON 6, NYLON 66, and C-113 NYLON available from Dupont. Examples of polyester fibers include polyester staple fibers commercially available from KoSa, Wellman Inc., and Syntec Industries Inc.

The assembly or network of no-bonded fibers can be air or wet-laid on a web and formed to the correct dimensions before the collection of fibers is introduced into a mold that is used to fabricate the cleansing article. Alternatively, the fibers can simply be added without prior air or wet laying to the hydrous composition or to the mold in which the fibrous bar is formed. In either event some of the fibers will form entanglements, that tend to hold the fibers in a network while the cleansing article is being used.

Another type of fabricated polymer network is a soft sponge formed from a woven material especially a soft diamond mesh polymeric scrim (a light-weight, open woven fabric). An example of one type of sponge is prepared from extruded tubular netting mesh, which is composed of smooth, flexible polymeric material. Extruded tubular netting mesh of this type, and particularly those prepared from polyethylene are readily available in industry.

The polymeric mesh sponge comprises a plurality of plys of an extruded tubular netting mesh prepared from a flexible polymer, preferably of the group consisting of addition polymers of olefin monomers, and polyamides of polycarboxylic acids and polyamines.

One way such tubular netting can be employed is to form a series of pleats by repeatedly folding the tube to form a 3-dimensional pad that can fit within a mold used to fabricate the cleansing article. Although the individual pleats can be unsecured, the "pad" so formed will unravel as the fibrous bar is used and the hydrous composition dissolves. Preferably, however, the pleats are secured by some type of bonding or closure to form a permanent 3-dimension pad or batt.

The bonding can be via thermal treatment (spot or strip welded) or by the application of adhesive (e.g., hot-melt). Alternatively, the pleats can be secured by a weaving or punch process or by any other suitable closure known in the art.

Examples of batts formed by pleating soft diamond mesh scrim are described in U.S. Pat. No. 5,412,830 to Girardot et al.

In the non-woven bonded or individual fiber FPN and the woven FPN described above, some or all of the individual fibers may be water-soluble. As used herein, "water-soluble" means that the fibers, disintegrate, or dissolve in water. Suitable materials for water soluble fibers include, but are not limited to, polyethylene oxide ("PEO"), blends of PEO and polypropylene as taught in United States Patent Application 2002/022691 A1, hereby incorporated by reference. Other examples include polylactic acid fibers sold under the tradename LACTRON® by Kanebo, polysaccharides sold under the tradename LYSORB® available from Lysac Technologies Inc., and polyvinyl alcohol such as those sold under the tradename KURALON K-II available from Kuraray Co., Ltd.

Another type of FPN is open cell foam fabricated from polyurethane, modified polyurethane or coated polyurethane. Although not physically a fibrous structure, the characteristics of open cell foam, especially reticulated open cell foam (cell paces essentially not present), have many aspects in common with non-woven fiber networks. As such, FPN formed from open cell polyurethane foams are included in the scope of "fibrous cleansing bars". Such foams are available in reticulated or non-reticulated forms. Of these forms flexible, reticulated, open-cell foams having a density between about 0.02 gm/cm$^3$ to about 0.03 gm/cm$^3$ are particularly suitable because they are soft, have a high void volume and are readily incorporated in the hydrous composition.

Modified polyurethanes include for example hydrophilic polyurethane formed by reacting an isethionate-terminated prepolymer formed from a hydrophilic polyol ether polyol, e.g., polyoxyethylene polyol and a polyisocyanate and with a water reactant. Such hydrophilic polyurethanes are described in U.S. Pat. No. 4,137,200.

As was the case of FPN based on fiber assemblies described above, synthetic sponges like open-cell foams can be pleated or corrugated in a variety of patterns. This can be accomplished by any suitable post-treatment such a compression thermal bonding. However, a more practical approach is by the direct molding of the foam in the shape and texture desired.

Preferably, for suitable lather generation of the inventive cleansing article, the density and therefore porosity (P) are important. Porosity can be defined as the volume fraction of air to polymer within a given FPN. Porosity can be expressed using following equation:

$$P = \frac{\rho_f - \rho_w}{\rho_f},$$

where $\rho_f$ is fiber (or polymer) density (g/cm$^3$) and $\rho_w$ is FPN density (g/cm$^3$). Note that the FPN density is based on the apparent thickness of the fabricated network structure. Preferably, the FPN of the present invention should display porosity in the range of from about 0.95 to 0.9999.

Another advantageous material property is the resiliency of the FPN assembly used in the present invention. Specifically, Percent Energy Loss is a desirable parameter as it describes the resilience of the network to an applied load. % Energy Loss is calculated as follows:

$$\% \, EnergyLoss = \left[\frac{J_T - J_R}{J_T}\right] * 100,$$

where $J_T$, is the Total Energy required to compress the FPN to a 100 gram load and $J_R$ is the Recovered Energy during one compression cycle (see Energy Loss Test Method described below). Lower energy loss is seen to correspond to a more resilient network. Preferably, FPN of the current invention have percent energy loss values ranging from about 5% to 50%.

Another useful property of the FPN is air permeability. Air permeability preferably is in the range of about 200 to 900 cubic ft/sq. ft/min (about 60 to about 275 m$^3$/m$^2$/min), more preferably of about 300-700 cubic ft/sq. ft/min (about 90 to about 212 m$^3$/m$^2$/min). Note that 1 cubic ft/sq. ft/min is equal to 0.304 m$^3$/m$^2$/min. Air permeability may be measured using the methodology described below Hydrous Lathering Composition The hydrous lathering composition forms a contiguous solid or semi-solid phase, which extends throughout the void volume of the fabricated polymer network, which it at least partially encompasses. By contiguous is meant that the hydrous composition is not simply trapped as isolated pools within the pores of the network as would be the case for a scrub or cleaning pads or filled sponge but rather is a continuous phase running throughout the at least partially encompassed FPN.

The hydrous composition comprises the majority of the cleansing article by weight. Thus, the ratio of the weight of the hydrous composition to weight of the FPN is in the range from about 30 to 1 to about 2000 to 1, preferably about 50 to 1 to bout 500 to 1, and most preferably about 75 to 1 to about 250 to 1.

The hydrous composition is preferably a solid of a hardness typical of toilet soaps (rheological characteristics often described as a "soft solid") or a semi-solid elastic material that has an adequate yield value to retain its shape and to be self supporting. In contrast, viscous pastes that are typically used in scrub or cleaning pads or filled sponge are outside the scope of the present invention.

When the hydrous lathering composition is in the form of a solid the composition should have a hardness value measured at a temperature at 25° C. of at least about 15 lbs/in$^2$ (103.4 kPa), preferably at least about 20 lbs/in$^2$ (139 kPa), and more preferably greater than about 25 lbs/in$^2$ (172.4 kPa) as measured by the Cylinder Impaction Test described in the Evaluation Methodology section below. To convert to SI units 1 lbs/in$^2$ is equal to 6.895 kPa.

The hydrous lathering composition can also be a semi-solid, preferably an elastic semi-solid. The term semi-solid as used herein designates structures that in the absence of a rigid container can keep the shape in which they have been molded or formed for long periods of time: typically days to months. However, they may be deformed and often exhibit viscoelastic behavior in shear deformation.

Semi-solids useful as the hydrous lathering composition of the present invention should have a yield stress expressed as the force per unit area required to cut or fracture the semi-solid composition. Generally, the composition of the present invention have a yield stress that is greater than about 10 kPa, preferably greater than about 15 kPa and most preferably greater than about 20 kPa.

By the term elastic is meant that the composition substantially returns to its original shape after a force is applied for a set time and then removed. Specifically, the surface of the hydrous composition when compressed to 80% of its thickness and held for 1 minute should be capable of returning to within about 5% of its original thickness within about 30 seconds.

The elasticity of the composition can be characterized by its elastic modulus, which is defined in the present context as the ratio of the force acting normal to a unit area and the linear displacement produced by this force. An alternative measure of elasticity is the compliance, which is the reciprocal of the elastic modulus, and represents the extent of deformation produced by a unit stress (e.g., pressure) acting normal to the surface of the semi-solid.

The compliance of the foamable composition is expressed as the displacement in millimeters produced by a 1 gram force acting over a 1 square centimeter area of gel. Compliance has units of $mm/gm/cm^2$ and can be converted into the SI units of M/Pa by multiplying by the factor $1.02 \times 10^{-4}$.

Since the compliance is a function of applied stress, a compliance at a stress value of 3.95 $gm/cm^2$ is a convenient measure for comparison of compositions as this represents the stress provided by a 20 gm force acting over 1 inch cylindrical platens (area 5.067 $cm^2$).

When the hydrous composition is in the form of an elastic semi-solid, the compliance should be in the range of from about 0.06 to about 1, preferably from about 0.07 to about 0.3 and most preferably from about 0.07 to about 0.2 $mm/gm/cm^2$ when measured at a stress value of 3.95 $gm/cm^2$.

The hydrous lathering composition includes hydrous component(s), one or more lathering surfactants, an organic benefit agent and various optional ingredients such as structuring agents, and adjuncts. These components are described below.

A. Hydrous Components

As the term "hydrous lathering composition" implies, a major component of the composition is ether water or a mixture of water and an optional water soluble organic solvent that forms the continuous phase of the hydrous lathering composition. The hydrous lathering composition should include water or a combination of water and an optional water soluble organic solvent at a level of at least about 40% by weight of composition, preferably at least about 45% by weight and more preferably at least about 50% by weight of composition.

The term "water soluble organic solvent" is used herein to describe a highly water soluble organic molecule that is innocuous to the skin in aqueous solution and can be used to manipulate the solubility of other organic molecules or alter the pliability, the clarity or properties of the composition. The water soluble organic solvent can be a liquid or a solid in its pure state. By highly water soluble is meant a water solubility in excess of 10% by weight, preferably in excess of 20% by weight and most preferably a solubility in excess of 50% by weight in water at room temperature.

One group of suitable water soluble organic solvents for use herein include $C_1$-$C_{10}$ mono- or polyhydric alcohols and/or their alkoxylated ethers. In these compounds, alcoholic residues containing 3 to 6 carbon atoms are preferred. Examples of this group include ethanol, isopropanol, n-propanol, butanol, propylene glycol, ethylene glycol monoethyl ether, hexylene glycol, glycerol, sorbitol and mixtures thereof.

Another group of water soluble organic solvents include polyalkylene oxides having a molecular weight below about 1000 Daltons. These include polyethylene oxide, polypropylene oxide, and random or block copolymers of ethylene oxide and propylene oxide alone or also containing butylene oxide and/or a terminal alcohol group having about 2 to about 8 carbon atoms.

Water soluble organic solvents can also be sugars and polysaccharides, especially low molecular weight polysaccharides (molecular weight less than about 25,000 daltons) such as sucrose, glucose, polydextrose, and maltodextrin.

Another type of but less preferred type of organic solvent is an alkanolamine such as triethanolamine.

Preferred water soluble organic solvents are selected from the group consisting of a C1 to C3 alcohols, monoethanolamine, triethanolamine, glycerol, propylene glycol, sorbitol, sucrose, polyethylene glycol and mixtures thereof.

The water soluble organic solvent(s) may be present at a level of from 0 to about 50%, preferably from about 2 to about 35% and most preferably from about 2% to 30% based on the total weight of the hydrous lathering composition.

B. Surfactants

Surfactant components provide lather and assist in the removal of soil and germs. The surfactant should be sufficiently mild to skin and eyes to be suitable for everyday use in cleaning the body in combination with the fabricated polymer network. A variety of surfactant classes discussed below can be employed in the invention.

Anionic Surfactants

Anionic surfactants may comprise about 2% to about 60%, preferably about 2% about 45% and more preferably about 5% to about 35% by weight of the hydrous composition.

Soluble soaps are one suitable type of anionic surfactant. Soluble soap is defined as a soap or soap blend having a Krafft point less than or equal to about 40° C. The soluble soap(s) can be selected from the chain length of $C_6$-$C_{14}$ saturated fatty acid soap(s) and $C_{16}$-$C_{18}$ unsaturated and polyunsaturated fatty acid soap(s) or a combination of these fatty acid soaps. Here the Krafft point of the soap is defined as the temperature at which the solubility of the soap rises sharply. These soluble soaps can be derived from coco fatty acid, Babasu fatty acid, palm kernel fatty acid and any other source of unsaturated fatty acid including tallow and vegetable oils and their mixtures. The soap may be prepared from coconut oils in which case the fatty acid content of $C_{12}$-$C_{18}$ is about 85% with $C_{12}$-$C_{14}$ species predominant. In addition to specific "soluble" soap, additional soap(s), which may not be as soluble, may be used. These soap components are here referred to as insoluble soaps. Such soaps are typically formed from saturated fatty acids having $C_{16}$-$C_{18}$ saturated hydrocarbon chains, The insoluble soap components can for example, be in the range of 5-20% as a structurant for the hydrous composition.

The term "soap" is used here in its popular sense, i.e., the alkali metal or alkanol ammonium salts of aliphatic alkane- or alkene monocarboxylic acids. Sodium, potassium, mono-, di- and tri-ethanol ammonium (TEA) cations, or combinations thereof, are suitable for purposes of this invention. In general, sodium soaps are used in the compositions of this invention, but from about 1% to about 25% of the soap may be potassium or TEA soaps. Overall the soap(s) useful herein are the well known alkali metal salts of natural of synthetic aliphatic (alkanoic or alkenoic) acids having about 12 to 22 carbon atoms, preferably about 12 to about 18 carbon atoms. They may be described as alkali metal carboxylates of hydrocarbons having about 12 to about 22 carbon atoms. The soaps may contain unsaturation in accordance with commercially acceptable standards. Excessive unsaturation is normally avoided to minimize the color and odor issues.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate or alkanolamide.

The hydrous composition of the present invention may contain one or more anionic synthetic detergents (syndets).

The anionic surfactant may be an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS).

The anionic may also be an alkyl sulfate (e.g., $C_{12}$-$C_{18}$ alkyl sulfate) or alkyl ether sulfate such as alkyl ethoxy (1-10 EO) sulfate and an alkyl glyceryl ether sulfate or a mixture of the two.

The anionic may also be $C_{10}$ to $C_{18}$, preferably $C_{12}$ to $C_{14}$ alkyl sulfosuccinates; alkyl and acyl taurates, alkyl and acyl sarcosinates, fatty N-acyl amino acid salts, sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sodium and ammonium alkylethoxy (1-5 EO) sulfosuccinates, especially lauryl ethoxy (3 EO) sulfosuccinate are also useful.

The hydrous composition may contain $C_8$-$C_{14}$ acyl isethionates. These esters are prepared by reaction between alkali metal isethionate with mixed aliphatic fatty acids having from 6 to 12 carbon atoms and an iodine value of less than 20.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids.

A further possibility is that the amphoteric surfactant is a sulphobetaine. A preferred sulfobetaine is cocoamidopropyl hydroxy sultaine Amphoacetates and diamphoacetates are also intended to be covered in the zwitterionic and/or amphoteric compounds which are used such as e.g., sodium lauroamphoacetate, sodium cocoamphoacetate, and blends thereof, and the like.

A preferred amphoteric surfactant is an alkyl betaine such as cocobetaine. or an alkylamidoalkyl betaine such as cocoamidoproyl betaine or When present, the level of amphoteric surfactant can be in the range from about 1% to about 15%, preferably from about 1% to about 10%, and most preferably from about 1.5% to about 8%.

Nonionic Surfactants

One or more nonionic surfactants may also be used provided they do not interfere with lathering or overall skin mildness or induce eye irritation. When present, nonionic surfactants may be used at levels from 1% to about 10%, preferably about 1% to about 5%, and most preferably from about 0.5% to about 4% by weight.

The nonionics which may be generally used include the reaction products of compounds having a hydrophobic group and a reactive hydrogen atom, for example aliphatic alcohols, acids, amides with alkylene oxides, especially ethylene oxide either alone or with propylene oxide. Examples of nonionic surfactants detergent compounds are ($C_{12}$-$C_{22}$) fatty alcohol-ethylene oxide condensates. However, alkylphenol-ethylene oxide condensates should be avoided because of their defatting properties.

The nonionic may also be a $C_{10}$ to $C_{16}$, preferably $C_{12}$ to $C_{14}$ fatty alkanol amide such as cocamide MEA. These nonionics are particularly effective foam boosting agents.

Other types of suitable nonionic surfactants are derived from saccharides or polysaccharides. These include $C_{10}$ to $C_{18}$ alkyl glycosides and alkylipolyglycosides which can be broadly defined as condensates of long chain alcohols, e.g., C8-30 alcohols, with sugars or starches, i.e., glycosides or polyglycosides.

Other useful nonionic surfactants include polyhydroxy fatty acid amide surfactants; specific examples of which include glucosamides such as coconut alkyl N-methyl glucosamide.

Other examples of nonionic surfactants are amine oxides such as dimethyldodecylamine oxide.

Cationic Surfactants

One or more cationic surfactants may also be used in the inventive foamable composition. Advantageously cationic surfactants are used from about 0.5 to about 10%, preferably from about 0.5% to about 5% by wt.

Examples of cationic surfactants are the quaternary ammonium compounds such as alkyldimethylammonium halides Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry and Berch, both of which are also incorporated into the subject application by reference.

C. Organic Benefit Agent

One benefit of the current invention relative to conventional soap or syndet bars is higher release of benefit agents that are hydrophobic and thus water insoluble or at most sparingly water-soluble (e.g., less than 0.5 wt %). By benefit agent is meant an organic molecule that provides some sensory or functional benefit that is delivered during or after the cleansing process. By the term release is meant the transference of the hydrophobic organic benefit agent from the aqueous cleansing phase in which the benefit agent is located to either the surface or interior of a different phase that is in contact with the aqueous phase. Typically, this different or adjacent phase is either the vapor phase or the surface of the skin. Thus, the hydrophobic organic benefit agents most relevant to the current invention provide either a fragrance benefit or are in some way beneficial to the skin.

A hydrophobic organic molecule is defined for purposes of the current invention as a molecule having an octanol/water partition coefficient ($\phi$)) of at least about 500, preferably greater than about 700, and most preferably greater than about 1000.

Preferred hydrophobic organic benefit agents are Type 2 and Type 3 perfume molecules as defined by Yang et al in U.S. Pat. No. 6,806,249 incorporated herein by reference. According to Yang et al the various types of perfume molecules are distinguished by their different combinations physico-chemical properties.

Type 2 perfume molecules are defined as those having an octanol/water partition coefficient, $\phi$, of at least about 500, preferably at least about 1000, and a volatility constant, K, less than about 20 Atm, preferably less than about 1.5 Atm. Here the volatility constant, K, is the proportionality constant between the concentration of a volatile solute in a solution (e.g., an aqueous solution) and the partial vapor pressure of the solute in a gas phase in equilibrium with this solution. Thus, K is recognized as the Henry law constant of a dilute solution.

Examples of Type 2 perfume molecules include but are not limited to allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, cinnamyl acetate, citronellyl acetate, citronellyl isobutyrate, citronellyl propionate, cuminic aldehyde, cyclohexylsalicylate, cyclamen aldehyde, cyclomyral, dihydro isojasmonate, diphenyl methane, diphenyl oxide, dodecanal, dodecalactone, ethylene brassylate, ethylmethyl phenylglycidate, ethyl undecylenate, exaltolide, Galoxilide® (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super® (7-acetyl,1,2,3,4,5,6,7,8-octahydro,1,1,6,7-tetramethyl napthalene), cis-jasmone, lilial, linalyl benzoate, 20 methoxy naphthaline, methyl cinnamate, methyl eugenol, methylionone, methyl linoleate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol, thibetolide, tonalid, δ-undecalactone, γ-undecalactone, vertenex, vetiveryl acetate, yara-yara and ylangene and mixtures of the above.

Type 3 perfumes are defined as those having an octanol/water partition coefficient, $\phi$, of at least about 500, preferably at least about 1000, and a volatility constant, K, greater than about 20 Atm and preferably in the range from about 20 Atm to about 1000 Atm.

Type 3 perfume molecules fall into the top and middle note catergory and include but are not limited to allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, mercenyl acetate, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, and verdox and mixtures of the above.

The value of K depends both on the interaction of the solute (perfume) with the solvent (water in this case) and its intrinsic volatility. Thus K can be estimated from the partition coefficient $\phi$, and boiling point, BP, of the perfume through correlation using known data, i.e., K=F($\phi$, BP).

Although we have chosen to use the Yang et al classification, it is noted that other classification schemes based directly on $\phi$ and BP can be utilized to classify perfumes (since K=F($\phi$, BP)) into for example hydrophobic variants of the well know "top note", "middle note" and "bottom note" categories. However, regardless of the scheme used the common feature of the perfumes that take optimal advantage of the release characteristics of the present invention is their hydrophobicity, e.g., $\phi$>500.

The Type 2 and Type 3 perfumes molecules can be used individually but more preferably in combination.

The total level of Type 2 and/or Type 3 perfume is between about 0.1% to about 5% by weight of hydrous composition, preferably between about 0.25% to about 4%, and most preferably between about 0.4% to about 3.5% by weight.

The second broad class of hydrophobic organic benefit agents are materials that provide benefits to the skin. Hydrophobic skin benefit agents include but are not limited to the following classes of benefit agents:

lipids that are useful in skin barrier function and repair such as cholesterol, ceramides, pseudoceramides, and precursor triglycerides (Sunflower and Borage seed oils);

antimicrobial agents such as 2-hydroxy-4,2',4'-trichlorodiphenylether (TRICLOSAN or ERGASAN DP300) and 3,4,4'-trichlorocarbanilide (TCC), Fat soluble vitamins, provitamins and vitamin precursors such as vitamin A, beta-carotene (provitamin A), vitamin B-3, vitamin E, and vitamin C-fatty alkyl esters;

UV A and UV B absorbers (sunscreens) such as octyl methoxy cinnamate (Parsol MCX) and butyl methoxy benzoylmethane (Parsol 1789), Anti-aging agents such as retinol esters, and fatty long chain alpha hydroxy acids.

antioxidants used to reduce photodamage and premature damage due to excessive oxidation such as ascorby palmitate, Vitamin E acetate, butylated hydroxyanisole and; 2,6-ditertiarybutylpara-cresol;

insect repellants such as N,N-dimethy-m-toluamide, 3-(N-butyl-Nacetyl)-aminopropionic acid, ethyl ester and dipropyl isocinchomeronate.

essential oils like bergamot, citrus unshiu, calamus, and the like.

Mixtures of any of the above These and other suitable hydrophobic skin benefit agents comprise from about 0.0001% to about 20%, more preferably from about 0.05% to about 15%, even more preferably 0.1% to about 10%, and most preferably 0.1% to about 5%, by weight of the hydrous composition.

It is finally emphasized that the compilations of organic benefit molecules given above are in no way meant to be exhaustive or limit the scope of the invention. Specific materials are named solely for the purpose of illustration. New perfume and skin benefit ingredients are continually being developed either through synthesis or by separation from natural products. By utilizing the principles and criteria described herein, one skilled in the art can now determine whether a particular material will be suitable for purposes of the present invention and the invention should be interpreted as encompassing such suitable materials.

D. Optional Ingredients

Structuring Agents

Structuring of the hydrous composition is often provided by the surfactants themselves. For example, interlocking networks of macroscopic crystals of soap may provide the structure. Such compositions are described in U.S. Pat. No. 5,340,492 to Kacher et al issued Aug. 23,1994, and in U.S. Pat. No. 6,363,567 to Nadakatti et al issued Apr. 2, 2002 both of which are incorporated herein by reference.

Another example of surfactant structured compositions are the "coagels" formed by networks of nano-crystals or by an isotropic liquid crystalline phase, e.g., cubic or gel phases. Nonlimiting examples of such compositions are described in U.S. Pat. No. 4,988,453 to Chambers et al issued Jan. 29, 1991 and U.S. Pat. No 5,310,485 to Hill et al issued May 10, 1994.

However, in some circumstances additional structuring agents prove useful and can be employed in the invention at levels between about 0.5% and about 15% by weight, preferably between about 1% and about 10% by weight. Such structurants include saturated, ($C_8$-$C_{18}$) fatty acids or ester derivatives thereof, substituted fatty acids, long chain, preferably straight and/or branched long chain, saturated, ($C_{13}$-$C_{24}$) alkyl alcohol, or $C_{19}$-$C_{24}$ alkenyl alcohols or mixtures thereof. Non-limiting examples include stearic acid, 12-hydroxystearic acid and cetostearyl alcohol. Non-limiting examples of the effective use of such structurants in thermosetting compositions are disclosed in U.S. Pat. No. 6,458,751 to Abbas et al issued Oct. 1, 2002.

Other useful structuring components are mono-di- and triglycerides especially hydrogenated glycerides such a hydrogenated cotton seed oil.

Mixtures of long chain fatty amines with anionic surfactants alone or admixed with fatty acid or fatty alcohol can also be employed as structurants.

Another class of useful structuring agents for semi-solid compositions is thermosetting polymers, i.e., polymers that form thermoreversible gels having a specific melting of gelling temperature. These polymers are particularly useful in the formulation of thermosetting elastic compositions. Non-limiting examples of useful polymers that form thermoreversible semi-solids include gelatin, carrageenan, agar, and gellan.

The incorporation of agents that provide some structure to the composition while it is still in the molten state is often very useful in the preparation of compositions that incorporate multiple phases. Such structurants suspend and prevent segregation of dispersed phases before the composition sets. Example of suitable structuring agents for gas bubbles are the PEG alkyl ester and PEG alkyl ethers such as PEG (12) monolaurate. Examples of thermosetting compositions utilizing such suspending agents for highly aerated bars are described in U.S. Pat. No. 5,972,860 to Eshita et al Issued Oct. 26, 1999.

Examples of other suitable structurants for suspension of for example, particulate inclusions are synthetic or natural hectorites. A synthetic hectorite, LAPONITE XLG from Laporte is particularly suitable. Examples of thermosetting compositions utilizing such suspending agents for suspending articles such as microcapsules in thermosetting compositions is disclosed in U.S. Pat. No. 6,403,543 to Edmund George issued Jun. 11, 2002.

Other structuring aids can also be selected from water soluble polymers chemically modified with a hydrophobic moiety or moieties, for example, EO-PO block copolymer, hydrophobically modified PEG such as POE(200)-glyceryl-stearate, glucam DOE 120 (PEG 120 Methyl Glucose Dioleate), and Hodag CSA-102 (PEG-150 stearate), and Rewoderm®(PEG modified glyceryl cocoate, palmate or tallowate) from Rewo Chemicals. Other structuring aids which may be used include Amerchol Polymer HM 1500 (Nonoxynyl Hydroxyethyl Cellulose) and hydroxypropyl starch phosphate sold by National Starch and Chemicals.

The hydrous composition can optionally contain fillers, which provide body or strength to the composition. Suitable fillers are selected from inorganic minerals such as calcium sulfate, sodium aluminates, and the like; starches, preferably water soluble starches such as maltodextrin and the like and polyethylene wax or paraffin wax, and the like. Fillers may be present in the composition in the range of about 1 to about 15% by weight, preferably about 1 to about 10% by weight.

Aesthetic and Adjunct Ingredients

A wide variety of optional ingredients can be incorporated in the foamable composition provided they do not interfere with the structuring, in-use properties of the composition (e.g., lather amount and rate), and release characteristics of the composition (e.g., perfume burst). These ingredients include but are not limited to: hydrophilic perfumes (Type 1 and Type 4); pearlizing and opacifying agents such as higher fatty acids and alcohols, ethoxylated fatty acids, solid esters, nacreous "interference pigments" such as $TiO_2$ coated micas; dyes and pigments; sensates such as menthol and ginger; preservatives such as dimethyloldimethylhydantoin (Glydant XL1000), parabens, sorbic acid and the like; anti-oxidants such as, for example, butylated hydroxytoluene (BHT); chelating agents such as salts of ethylene diamine tetra acetic acid (EDTA) and trisodium etridronate; emulsion stabilizers; auxiliary thickeners; buffering agents; skin conditioning agents such as silicones (e.g., Dimethicone), hydrocarbon (e.g., petrolatum) and cationic polymers (e.g., cationic guars and cellulosics), and mixtures thereof.

Manufacturing and Packaging

The fibrous bars of the invention are preferably made by a melt and pour (also called "melt-cast") process in which the molten hydrous lathering composition is combined with and at least partially encompasses the fabricated polymer network and is then allowed to solidify or gel, i.e., by reducing the temperature to below the melting point.

This process can be carried out in several ways. In one preferred embodiment, the combining step is carried out in a single-use mold where the mold forms all or a part of the package in which the fibrous bar is sold or even stored during use. A description follows.

Two broad types of single-use molds, well known in the art, can be employed. The first is made up of two or more individual parts that are preassembled (press fitted or glued) into a "unitary design" before filling it with the molten hydrous composition. In this case, the FPN can be inserted into the mold either before or after the mold is assembled. Here, the molten composition is injected or poured into the mold, and then the mold entry is sealed by either heat sealing or with a separate covering (e.g., a polymer film). Such a mold can be filled either along one of its edges or along its face.

The second type of single-use mold is a "blister pack" formed by shaping a polymer film (e.g., blow molding or stretching over a mandrill) into a cup-like structure. Here, the FPN can be inserted into the mold before or after the molten hydrous composition is added. Furthermore, the bottom of the cup can have either a protrusion or well that accommodates a part of the fibrous layer, or can have an elevated or depressed area that provides an indicia or logo to the fibrous bar. Once the blister pack is filled, the pack is sealed and cooled (not necessarily in this order). The sealing is generally accomplished by covering with a polymer, paper or laminated film: sealing provided via some form of adhesive or by heat or pressure sealing.

Either the unitary design or blister pack mold can be subjected to lower temperature cooling to accelerate the setting of the composition. The cooling can be accomplished either in bulk storage (e.g., a refrigerator) or by passage through a cooling chamber such as a cooling tunnel. The single use mold can serve as the final package at point of sale and thus bears printing or a means for hanging or display. Alternatively, the mold can be further wrapped or cartoned.

A second suitable processing route employs a multiple-use mold wherein the fibrous bar is formed and solidified in the mold, released from the mold for further processing. In this case the mold is reused. A disposable mold can also be used to accomplish the same processing ends—the mold being discarded after the article is demolded. In any event, the molten hydrous composition is added to the mold by gravity or pressure feeding (injection). The mold can be of such a shape and volume so as to form either a single fibrous bar or it can be a tray, pan, or cylinder so as to form a loaf, log or billet that can be cut into individual articles. Alternatively, the mold can include two or more elements that are joined before the foamable composition is introduced (e.g., by injection under pressure) and then separated after the composition has set to release the article. Such an "injection mold" can form either an individual fibrous bar or a log or loaf that can be cut after demolding. The setting process can be accomplished continuously, for example by chilling the mold, or the molds can be stored for a suitable period of time in a chamber at any temperature below the melting or setting point of the composition and later the article can be demolded.

The FPN can be inserted into the multiple-use mold before or after the molten hydrous composition and the mold can also include a recessed area to accommodate part of the fibrous layer. Alternatively, the mold can be partially filled and the foamable composition partially set before the fibrous layer is introduced.

Once set, the fibrous bar is demolded and further processed and packed. For example, the article can be further shaped (e.g., by cutting), wrapped in a film (e.g., shrink-wrapped), cartoned or any combination of such steps.

In either of the manufacturing methods described above, the hydrous lathering composition can be partially cooled, for example by means of an in-line heat exchanger before the composition is inserted into the mold and combined with the FPN.

Evaluation Methodology

A. Percent Energy Loss Test Procedure:

Percent Energy Loss describes the resilience of a network to an applied load. A 3.8 cm circular disk of the test FPN is placed between the platens of an Instron Tensile/Compression Testing Machine (e.g. Instron Model No 4501 with load cell (226.98 N load Cell). The platen separation is 31.75 mm. The sample is then compressed at a compression cycle strain rate of 38 mm/min to a maximum load of 100 gm-force (0.98N) using a 5N load cell. The platens are then separated at a recovery cycle strain rate of 38 mm/min.

Total Energy required to compress a sample to 100 grams load, and the Recovered Energy from one compression cycle is determined. The % Energy Loss is then calculated as follows:

$$\% \, Energy Loss = \left[\frac{J_T - J_R}{J_T}\right] * 100$$

% Energy Loss is the resiliency of the FPN i.e. the ability to recover compressive force
$J_T$=Total Energy Required to Compress material to 100 grams
$J_R$=Recovered Energy during one compression cycle B. Yield Stress—Cheese Cutter Method for semi-solids This method measures the yield stress of composition and is used herein a to measure the maximum strength of an elastic semi-solid. This method can also be used to measure the yield stress of the composition, i.e., the foamable composition that includes the fibrous layer.

A wire penetrating into the cleansing material with a constant force will come to rest when the force on the wire due to internal stress balances the weight applied to the wire. The stress at the equilibrium point is described as yield stress ($\sigma_o$). The procedure is as follows.

A square of test sample (3.2 cm×3.2 cm×5 cm) is positioned on the yield stress device. A 400-grams weight is then attached to the arm of the device. The arm is then lowered such that the wire comes into contact with sample. The arm is then released allowing the wire to penetrate the test sample for 1 minute. The length of wire in the sample is then measured and recorded. The yield stress ($\sigma_o$) in kPa is determined from the following equation:

$$\sigma_o = \frac{0.375 \, mg}{lD},$$

where,
m=mass of driving wire (mass placed on device plus 56 grams)
g=gravitational constant (9.8 m/s$^2$)
l=length of wire measured to penetrate the semi-solid after 1 minute (mm)
D=diameter of wire (e.g., 0.336 mm)

C. Instron Indentation Test—for Compliance of Elastic Semi-solids

This method is used to measure the compliance (linear displacement per unit of stress at a give stress value (force per unit area)) of elastic hydrous lathering compositions composition. Softer compositions are those which have a greater compliance.

The compliance is computed from measurements of the depth of indentation (displacement) as a function of applied load of a rod into a "block" formed from the semi-solid elastic gel composition (or a composite that also includes the FPN). The displacement as a function of load is measured using an Instron Model 4501 Universal Testing Instrument.

Two blocks (typically 3.2 cm×3.2 cm×5 cm) of each composition are prepared and equilibrated in an environmental chamber at 21° C. and 50% relative humidity prior to testing. A 2.54 cm diameter indenting plate coupled to the Instron is then pressed against each block at a rate of 25 mm/min and recorded the forces at 50 data points per minute until a compression force of 65 grams is reached. The data is then transformed into the displacement at 5, 10, 20, 30 and 50 grams force applied load. Each block is compressed six times at different locations on the block.

The compliance at each applied stress in computed from:

Stress=Load (gm-force)÷Area of identing plate (cm²)

Compliance=Displacement of indenting plate (mm)÷ Stress (gm/cm²)

D. Air Permeability Methodology

The Air Permeability is related to the amount of lather that can be generated by a particular fabricated polymer network. The Air Permeability has been found to directly affect the density and amount of lather that a particular nonwoven material is capable of generating. The Air Permeability values of the present invention were determined using ASTM Method—Designation D 737-96.

Testing Components:
1. Test head that provides a circular test area of 38.3 cm 2±0.3%;
2. Clamping system to secure test specimens;
3. A clamping ring that minimizes edge leakage;
4. Air flow controller providing a minimum pressure drop of 125 Pa (12.7 mm or 0.5 in. of water) across the specimen);
5. Pressure gauge or manometer having an accuracy of ±2%;
6. Flowmeter, volumetric counter or measuring aperture to measure air velocity through the test area in cm 3/s/cm 2 (ft 3/min/ft 2) with an accuracy of ±2%;
7. Calibration plate, or other means, with a known air permeability at the prescribed test pressure differential to verify the apparatus;
8. Means of calculating and displaying the required results, e.g., scales, digital display, and computer-driven systems; and
9. Cutting dies or templates, to cut substrate specimens having dimensions at least equal to the area of the clamping surfaces of the test apparatus.

The FPN samples are cut to the appropriate size (size of clamping surface) using a cutting die. The samples are then preconditioned at a standard temperature and humidity, 21° C.±1° C. and 65±2% R.H. Once the samples are preconditioned, they are allowed to reach moisture equilibrium in the standard atmosphere. The test samples are carefully handled to avoid altering the natural state of the samples. They are then place in the test head of the test apparatus, and the test is performed as specified in the manufacturer's operating instructions. The tests are carried out using a water pressure differential of 125 Pa (12.7 mm or 0.5 in. of H₂O). The individual test sample results are recorded in ft³/min/ft² (or 0.304 m³/min/m² in metric units) These results represent the Air Permeability of the samples.

E. Fiber to Fiber Bond Determination (for Non-woven FPN)

A 4 mm×25 mm×25 mm section of nonwoven sample is prepared and placed on glass slide and secured with tape (sample slide). A reference glass slide is prepared by placing a 1 mm×1 mm mark on a glass surface. Photomicrographs of the reference slide are taken at a 10× magnification and the length of mark on photo in mm is measured and recorded. Photograph (×5) of the sample slide are then taken under the microscope at 10× magnification. This is repeated for three other samples with each sample done in duplicate. The number of fiber to fiber bonds on each photo is then counted. Using a scale created from the reference slide, the actual area of each sample slide is determined. The number of fiber-to-fiber bonds is divided by the actual area (mm²) and the results finally averaged to provide the Number of Fiber-to-Fiber Bonds/mm³.

Each image can be expressed as a given volume V, using as a thickness one fiber diameter. Assuming perfect fiber packing and no air voids between fibers. Given a porosity (P), where porosity is the volume fraction of fiber to air in a given nonwoven sample, the number of contacts per cubic millimeter for a given nonwoven having porosity P can be calculated as follows.

The Image Volume (V) is Given by:

Volume (V)=image area (mm²)*fiber diameter(mm)

The Number of Fiber to fiber bonds per mm³ (TC) is calculated from:

$TC=CP/V$ where CP is the number of fiber to fiber bonds taken from sample image.

The actual number of fiber to fiber bonds (AC) is then determined from the following equation:

$AC=TC*(1-Porosity)$

F. SPME Analysis of Fragrance Retention

Fragrance retention on skin was measured by Solid Phase Micro Extraction (SPME). A slurry of the test article is prepared by combining 0.5 g of the composition with 1 ml of deionized water in a sealed container and stirring the mixture at about 30 to 35° C. for 30 minutes.

The forearm of a test subject was prewet with water at a temperature of 32° C. after which the entire sample of the slurry is applied with a gloved hand and the slurry was worked into a lather by gentle rubbing for 30 sec. The arm is then rinses for 15 minutes and patted dry with soft absorbent paper.

A closed bulb shaped collection vessel (approximate dimensions 2 cm in diameter by 50 cm high) containing a Supelco SPME Fiber Assembly (30 um DVB/Carboxen/PDMS) is secured in contact with the forearm and perfume in the head space was collected for 30 minutes. The procedure is repeated but after allowing the treated forearm to remain uncovered for 60 minutes.

The SPME fibers were analyzed by gas chromatography using an Agilant Technologies (formerly Hewlett Packard) Model 6890 with Mass Selective Detector Model 5973. A The column an Agilant Technologies number 19091S433, HP-5MS, 5% Phenyl Methyl Siloxane, 30 m×0.25 mm ID with a 0.25 μm film thickness.

G. Cylinder Inpaction Test for Hardness/yield Stress of Solids

A variety of methods are known in the art to measure the hardness of "soft solids" used in, for example, toilet soaps. The most common techniques are the Cylinder Impaction Test which measures the maximum force before yielding and the Penetration Test which measures the penetration of a needle under a constant load. Although the invention is described by parameters that are measured by the Cylinder Impaction Test, this was done for convenience from a manufacturing perspective. The various hardness tests can obviously be inter-correlated.

The Cylinder Impaction Test employs a modified Crush-Test protocol that is used for measuring carton strength. A Regmed Crush Tester was employed.

Samples of the solid hydrous lathering composition (typically 8×5×2 cm) at the desired temperature were placed on the lower plate of the tester fitted with a pressure gauge and a temperature probe inserted in the sample approximately 4 cm from the test area. An 89 gm inox metalic cylinder (2.2 cm in diameter (0.784 in) and 3 cm in length (1.18 in)) was placed at a central location on the top of the sample. The upper plate is then lowered to just touch the cylinder.

The top plate was then lowered at a programmed rate of 0.635±0.13 mm/s (0.025±0.005 in/sec). At a certain strain, the sample will yield, bend or fracture and the maximum force expressed as PSI (lbs/inch$^2$) and average sample temperature are recorded. The water content of the sample is measured immediately after the test by microwave analysis. The hardness measurement is repeated a total of 3 times with fresh samples and an average taken. It is important to control the temperature and water content of the sample since hardness is sensitive to both these variables.

H. In-vitro skin Retention Test—for sunscreen deposition

The retention of the sunscreen, e.g., PARSOL MCX, on skin washed with fibrous bars is estimated using an adaptation of the In-vitro Skin Retention Test as described U.S. Pat. No. 6,645,511 to Aronson et al.

A sample of porcine skin (3 to 4 weeks old female) used as the substrate is washed with 15% NaLES (sodium ethoxy (3 EO) sulfate) solution, rinsed with tap water, patted dry and shaved. The skin is cut into pieces approximately 4 cm by 9 cm and stored in the freezer for later use.

The test procedure and is as follows:

A 4×9 cm sample of skin that has been rinsed with warm tap water for 10 seconds. 1,100 micrograms of test solution (10% "solution" each test article in distilled water) is applied and rubbed in a circular motion on the skin for 30 seconds. This amount of solution corresponds to a dosage of 3 micrograms of bar composition per square centimeters of skin. The skin is then rinsed with tap water for 30 seconds at a flow rate delivering 13.5 g to 13.8 g of water per second at a temperature of 30° C. and patted dry with a paper towel. After air-drying for 5 minutes, A glass ring of 3 cm in diameter is placed tightly on the skin and 5 mL of heptane are dispensed into the ring while holding the ring tautly. The heptane is mixed on the skin with a transfer pipette by slowly squeezing the pipette repeatedly for 2 minutes and 30 seconds. The heptane is transferred from the ring to a small capped vial. The extraction process repeated 7-9 times giving a total of approximately 10 mL of heptane in each vial. After weighting the vial, the Parsol MCX concentration in the heptane extract is determined with a UV spectrometer (Biorad GS 700) using a 1 cm cell and a wavelength 900 to 1900 Nm.

The percent of oil retained on the skin is calculated using the following equation and recorded as % retention of oil after rinsing.

Oil Retention Index =

$$\frac{\text{Amount of } Parsol\ MCX \text{ extracted per cm}^2 \text{ of porcine skin}}{\text{Amount of } Parsol\ MCX \text{ dosed per cm}^2 \text{ of porcine skin}}$$

EXAMPLES

The following examples are shown as illustrations of the invention and are not intended in any way to limit its scope.

Example 1 and Comparative 1

The hydrous compositions of the exemplary and comparative fibrous bar are shown in Table 1A. The hydrophobic organic benefit agent is a perfume that includes both Type 2 and Type 3 perfume molecules.

TABLE 1A

Lathering Compositions of Example 1 and Comparative 1

| COMPONENT (as 100% active) | Ex 1 Wt % | C 1 Wt % |
|---|---|---|
| Sodium Cocoyl isethionate |  | 20.2 |
| Ammonium Lauryl Sulfate | 10.1 |  |
| Ammonium Laureth Sulfate 2EO (70%) | 7.9 |  |
| Cocamide MEA | 1.7 |  |
| PEG-5 Cocamide MEA | 0.9 |  |
| Cocamidopropyl Betaine | 10.0 |  |
| Sodium soap (65/35 tallow/cocco) |  | 54.6 |
| sodium isethionate |  | 5.6 |
| Polyquaternium-55 | 0.5 |  |
| Jaguar C13S | 0.5 |  |
| Gelatin Bloom 275 | 12.00 |  |
| Fatty acid |  | 6.8 |
| Perfume (includes Type 2 and Type 3 perfume molecules) | 0.8 | 0.8 |
| Minors (e.g., color preservatives, etc) | 1.7 | 3.5 |
| WATER SOLUBLE ORGANIC SOLVENT |  |  |
| Glycerin USP | 11.0 |  |
| Polyethylene Glycol 6000 | 1.0 |  |
| Water | 41.9 | 9.3 |
| Vol % Fabricated Polymer Network (Non-woven SF3) | 88 | 0 |
| Water + water soluble organic solvent | 53.9 | 9.3 |

The fabricated polymer network was a 100% polyethylene terephthalate non-woven, designated SF-3 (X-87), obtained from Structured Fibers Incorporated, Saltillo, Miss. The fibrous network is characterized by the parameters given in Table 1B.

TABLE 1B

Characteristics of fibrous network used in Ex 1

| Denier | % |
|---|---|
| 4 | 25 |
| 6 | 75 |
| Fiber Type | 100% PET |
| Basis Weight (oz/sq. yd)* | 5 |
| Number of fiber to fiber bonds per cubic mm | 2.19 |

Note
*Oz/sq. yd = 33.9 gm/m$^2$

To prepare Ex 1, approximately 100-grams of the hydrous lathering composition of Table 1A in the molten state at temperatures ranging from 45° C. to 65° C. was poured onto the FPN (Table 1B) contained in a mold and allowed to totally absorb and completely permeate the network. The hydrous composition was combined with perfume and poured at the lowest temperature possible to minimize loss or degradation of perfume. The resulting intimately blended hydrous composition and FPN was cooled to about 15° C. at approximately 50% RH until solidified and the solidified article (bar shaped) was removed from the mold.

Comparative C1 was prepared by a conventional extrusion and stamping process well known in the art. The perfume was added immediately before extrusion via a ribbon mixer to minimize loss.

The perfume retention on forearms washed in a controlled manner with the Ex 1 and C1 cleansing articles was measured by the SPME method described in EVALUATION METHODOLOGY SECTION.

The perfume retention after 30 minutes measured on forearms washed with Ex 1 was 950 units while retention on forearms washed with the soap bar was 550 units. Thus, after 30 minutes about 70% more perfume was retained on the skin. Furthermore, perfume was still detectable on forearms washed with the exemplary bar even after an hour while essentially no fragrance was detectable by SPME in the case of the C1 washed forearms. These differences were self-perceivable at both time points and are highly statistically significant.

Thus, the cleansing article of the invention provided a distinct perceivable benefit in terms of the fragrance retention on skin relative to a conventional cleansing bar.

Example 2 and Comparatives 2 and 3

The hydrous lathering compositions that may be used to make cleansing articles are shown in Table 2. The hydrophobic organic benefit agent includes both Type 2 and Type 3 perfume molecules. The amount of sodium hydroxide employed in the Ex 2 composition is sufficient to neutralize about half of the fatty acid present: total surfactant concentration is approximately 21.3%

TABLE 2

Lathering Composition of Example 2 and Comparatives 2 and 3

| COMPONENT (as 100% active) | Ex 2 | C2 | C3 |
|---|---|---|---|
|  | Wt % |  |  |
| Stearic acid/palmitic acid blend | 14 |  | 14 |
| Coconut fatty acid | 9 | 4 | 9 |
| 12 hydroxy stearic acid | 3.5 |  | 3.5 |
| Lauric acid | 3.06 |  | 3.06 |
| Sodium lauryl sulfate | 7.20 |  | 7.20 |
| Sodium soap (85/15 tallow/cocco) |  | 80.0 |  |
| Sodium hydroxide | 2.34 |  | 2.34 |
| WATER SOLUBLE ORGANIC SOLVENTS |  |  |  |
| Sorbitol | 14.5 |  | 14.5 |
| Polyethylene Glycol (CARBOWAX 200) | 5.0 |  | 5.0 |
| Propylene glycol | 10.2 |  | 10.2 |
| Isopropyl alcohol | 1.23 |  | 1.23 |
| Glycerin |  | 0.2 |  |
| Perfume (includes Type 2 and Type 3 perfume constituents) | 1.8 | 1.8 | 1.8 |
| Minors (e.g., color preservatives, etc) | 1.94 | 0.5 | 1.94 |
| Water | 26.2 | 13.5 | 26.2 |
| Wt bar composition per gm Fibrous network (SF3) | 100 | — | — |
| Vol % Fabricated Polymer Network (Non-woven SF3) | 90 | — | — |
| Water + water soluble organic solvents | 57.1 | 13.5 | 57.1 |

The same non-woven FPN as used in Example 1, may be used here as well.

The Ex2, and C3 articles may be prepared by a melt-cast process as described under Ex1. C2 is prepared by a conventional extrusion and stamping process. The perfume is added immediately before extrusion via a ribbon mixer to minimize perfume loss.

The perfume retention on forearms washed in a controlled manner with the Ex2 and the C2 and C3 cleansing articles is measured by the SPME method.

The amount of perfume that is retained on the forearm 30 minutes after controlled washing with the exemplary article, Ex 2, is over twice that retained on forearms washed with the comparative article C2. Furthermore, perfume should still be detectable on forearms washed with the exemplary bar even after 1 hour while essentially no fragrance is detectable by SPME in the case of the C2 washed forearms. These differences are self-perceivable at both time points.

Thus, the fibrous bar of the invention provides a distinct perceivable benefit in terms of the fragrance retention relative to a conventional cleansing bar.

The exemplary fibrous bar, Ex 2 is compared with the comparative article C3 by a panel of 25 males who are soap bar users (ages 16-24) in a 2 week sequential monadic design. The exemplary article containing the non-woven is judged to leave the skin smelling fresher and more pleasant and to be more refreshing to use than the comparative cleansing bar without the fabricated non-woven polymer network.

Example 3 and Comparatives 4 and 5

Hydrous lathering compositions are shown in Table 3. The FPN (non-woven) that may be used is the same as that used in Example 1.

TABLE 3

Composition of Example 3 and comparatives 4 and 5

| COMPONENT (as 100% active) | Ex 3 | C4 | C5 |
|---|---|---|---|
|  | Wt % |  |  |
| Stearic acid/palmitic acid blend | 14 | 14 | 14 |
| Coconut fatty acid | 9 | 9 | 9 |
| 12 hydroxy stearic acid | 3.5 | 3.5 | 3.5 |
| Lauric acid | 3.06 | 3.06 | 3.06 |
| Sodium lauryl sulfate | 7.20 | 7.2 | 7.2 |
| Sodium soap (85/15 tallow/cocco) |  |  | 24 |
| Sodium hydroxide | 2.34 | 2.34 | 2.34 |
| WATER SOLUBLE ORGANIC SOLVENTS |  |  |  |
| Sorbitol | 14.5 | 2.16 | 0.5 |
| Polyethylene Glycol (CARBOWAX 200) | 5.0 |  | 5 |
| Propylene glycol | 10.2 | 5 | 10.2 |
| Isopropyl alcohol | 1.23 | 1 | 1.23 |
| Sunflower seed oil |  | 17 |  |
| Petrolatum |  | 1 |  |
| Stearyl alcohol |  | 2 |  |
| Hydrogenated cotton seed oil |  | 4 |  |
| Perfume (includes Type 2 and Type 3 perfume constituents) | 1.0 | 1.0 | 1.0 |
| Minors (e.g., color preservatives, etc) | 1.94 | 1.94 | 1.94 |
| Water | 26.2 | 25.0 | 17 |
| Wt bar composition per gm Fibrous network (SF3) | 100 | 100 | 100 |
| Vol % Fabricated Polymer Network (Non-woven SF3) | 90 | 90 | 90 |
| Water + water soluble organic solvent | 57.1 | 33.1 | 33.9 |

The Ex3, C4, C5 articles may be prepared via a melt cast as previously described. The C4 bar composition additionally includes sunflower seed oil, petrolatum, stearyl alcohol, and hydrogenated cottonseed oil. These materials are dispersed (emulsified) in the hot molten composition by means of overhead stirring. The composition is then cooled to 50° C. before the perfume is added.

The perfume retention on forearms washed in a controlled manner with the Ex 3 and the C4 and C5 cleansing articles may be measured by the SPME method.

The amount of perfume that is retained on the forearm 30 minutes after controlled washing with the exemplary article, Ex 3, is expected to be significantly higher than is retained on forearms washed with the comparative articles C4 or C5. Furthermore, perfume should be still detectable on forearms washed with the exemplary bar even after 1 hour while essentially no fragrance should be detectable by SPME in the case of the arms washed with the C4 and C5 comparative articles. These differences should be self-perceived at both time points.

Examples 4-6 and Comparative 6

The hydrous lathering compositions are shown in Table 4. The FPN is the non-woven of Example 1 and the melt cast process previously described may be used to make the articles.

TABLE 4

Composition of Example 4-6 and Comparative 6

| COMPONENT (as 100% active) | Ex 4 | Ex 5 | Ex 6 | C6 |
|---|---|---|---|---|
| | | Wt % | | |
| Sodium soap: (33/67 Tallow/Coco) | 30 | 30 | | |
| Sodium soap (77% hardened tallow/15% coconut/8% castor) | | | 33 | |
| Sodium soap: (85/12 Tallow/Coco | | | | 61.4 |
| Tea Soap (77% hardened tallow/15% coconut/8% castor) | | | 21 | |
| Coconut fatty acid | | | | 1.25 |
| Sunflower seed oil | | 10 | | |
| Petrolatum | | 1 | | |
| Stearyl alcohol | | 2 | | |
| Hydrogenated cotton seed oil | | 3.2 | | 2 |
| 12 hydroxy stearic acid (not neutralized) | | | | 3.5 |
| WATER SOLUBLE ORGANIC SOLVENTS | | | | |
| Sucrose | 25 | 17 | | |
| Sorbitol | 10 | 8 | | |
| Ethanol | 10 | 8 | | |
| CARBOWAX 200 (PEG) | | | | 2 |
| Glycerol | | | 10.8 | 12 |
| Triethanolamine | | | 22.8 | |
| Perfume (includes Type 2 and Type 3 perfume constituents) | 1 | 1 | 1 | 1 |
| Minors (e.g., color preservatives, etc) | 2 | 2 | 2 | 1.8 |
| Water | 22 | 17.8 | 9.4 | 15.8 |
| Wt bar composition per gm Fibrous network (SF3) | 100 | 100 | 100 | 100 |
| Vol % Fabricated Polymer Network (Non-woven SF3) | 90 | 90 | 90 | 90 |
| Water + water soluble organic solvent | 67 | 50.8 | 43 | 29 |

The perfume retention on forearms washed in a controlled manner with the Ex 4-6 and C6 is measured by the SPME method.

Even thought all the compositions in Table 4 contain the same level of perfume, the amount of perfume that is retained on the forearm 30 minutes after controlled washing is expected to fall in the order:

Ex4>Ex5>Ex6>>C4

Perfume is still detectable after 1 hour especially in the case of Ex 4 and Ex 5 but is not detectable for skin that is washed with the comparative C6 article.

It should be noted that the Ex 4, Ex 5 and Ex 6 hydrous compositions contain the same level of surfactant and perfume, yet Ex 4 article having a combined water and water soluble organic solvent level of over 60% provides a significantly higher level of perfume retention on skin.

Examples 7-11

These Examples Illustrate Different Fibrous Network.

The hydrous lathering composition of Ex 2 (Table 2) is used to prepare fibrous bars that employ the different fibrous networks identified in Table 5. These networks are composed of non-woven bonded fibers that differ in porosity and resiliency as defined by the methods described in the EVALUATION METHODOLOGY section. The individual fibrous cleansing bars are prepared by pouring the molten foamable composition into a mold that contained the non-woven layer and then solidifying the composition at about 15° C. as discussed in Example 1. The resulting fibrous bars, all of which should have a shape similar to a conventional soap bar, are characterized in Table 6.

TABLE 5

Non-woven fabrics used in fibrous bars of Examples 7-11

| | Non-Woven (FPN) | | | |
|---|---|---|---|---|
| Designation | Supplier | Porosity | Resiliency % Energy Loss | Material of Construction |
| LP Den | Legget & Platt Salisbury, NC | 0.9835 | 39.8 | PET |
| CAR 3 | Carlee Corp. Northvale, NJ | 0.9970 | 41.85 | PET |
| Kimberly Clark | K-C Corp. Neenah, WI | 0.9943 | 42.12 | PET |
| SF3 | Structured Fibers Saltillo, MS | 0.9951 | 15.79 | PET |
| CAR 2 | Carlee Corp. Northvale, NJ | 0.9970 | 39.82 | PET |

TABLE 6

Description of cleansing articles of Examples 7–11

| | Ex 7 | Ex 8 | Ex 9 | Ex 10 | Ex 11 |
|---|---|---|---|---|---|
| Non-woven fibrous layer | LPDEN | CAR3 | KC | SF3 | CAR2 |
| Weight of hydrous composition (Table 1) per fibrous bar (gm) | 100 | 100 | 100 | 100 | 100 |
| Weight of non-woven (Table 4A) per fibrous bar (gm) | 1 | 1 | 1 | 1 | 1 |
| Weight ratio of hydrous composition to FPN | 100 to 1 | 100 to 1 | 100 to 1 | 100 to 1 | 100 to 1 |

Incorporation of all of the non-woven materials should result in fibrous bars that have good integrity and provide lather during use. However, the amount of lather is expected to depend both on the porosity and the resiliency of the fibrous layer. More resilient structures should maintain adequate dimensional stability over time and over larger number of uses compared to samples that have comparatively poorer resiliency. Specifically, the Percent Energy Loss appears to be an important parameter as it describes the resilience of the substrate to an applied load. Lower energy loss corresponded to a more resilient fibrous substrate with better in-use properties.

Although all the above examples are robust and provide lather, Ex 10 which displays the lowest % energy loss values and hence is the most resilient of the fibrous layers tested provides the highest lather.

Example 12

A fibrous bar may be prepared using the hydrous lathering composition of Ex 2 and an FPN composed of entangled discrete fibers. The network is an entangled mass composed of 6 den PET fibers approximately 3.8 cm in length. Specifically, 1 gm of air-laid entangled fibers (Style #295 supplied by KOSA Inc.) may be placed in an empty plastic soap mold. 100 gm of the Ex 2 composition would then be melted and poured into the mold. The mold would then be cooled to room temperature, stored overnight and the fibrous bar removed.

Articles that incorporate a fibrous network of entangled discrete fibers are expected not to provide as much lather as articles employing a continuous network of bonded fibers such as is used in Ex 2. The article of Ex 12 nevertheless should provide enhanced perfume release and retention on skin.

Example 13

A fibrous bar may be prepared using the hydrous composition of Ex 2 and a FPN consisting of a batt made by folding and pleating a soft NYLON Scrim netting as described by Girardot et al in U.S. Pat. No. 5,412,830. The pleats are secured by knitting. The following procedure may be used:

98 gm of the Ex 2 composition is melted and poured into the PVC plastic mold. The batt is then added to the molten composition in the mold such that the batt is partially exposed. The mold is cooled to room temperature, stored overnight and the fibrous bar removed.

Articles that incorporate this type of diamond mesh batt are expected not to provide as much lather as article employing a continuous network of bonded fibers such as is used in Ex 2. The article of Ex 13 nevertheless should provide enhanced perfume release and retention on skin.

Example 15

A cleansing article may be prepared using the hydrous composition of Ex 2 and a FPN consisting of an open cell reticulated polyurethane foam. The foam, SIF® from Foamex has a porosity of 3 pores per inch and a density of 1.2 lb/ft$^3$. The following procedure may be used:

100 gm of the Ex 2 composition is melted and poured into the PVC plastic mold containing a stack of several sheets of polyurethane foam (7.0 cm×20 cm). The mold is cooled to room temperature, is stored overnight and the cleansing article is removed.

Articles that incorporate this type FPN are expected not to provide as much lather as an article employing a continuous network of bonded fibers such as is used in Ex 2. The article of Ex 13 nevertheless should provide enhanced perfume release and retention on skin.

Example 16 and Comparative 7

The hydrous lathering compositions that may be employed are shown in Table 3. The hydrophobic organic benefit agent is in this case a commonly used UV absorber (sunscreen) octyl methoxy cinnamate, commercially available as PARSOL MCX.

TABLE 7

Composition of Example 16 and comparatives 7

| COMPONENT (as 100% active) | Ex 16 Wt % | C7 |
|---|---|---|
| Stearic acid/palmitic acid blend | 14 | 14 |
| Coconut fatty acid | 9 | 9 |
| 12 hydroxy stearic acid | 3.5 | 3.5 |
| lauric acid | 3.06 | 3.06 |

TABLE 7-continued

Composition of Example 16 and comparatives 7

| COMPONENT (as 100% active) | Ex 16 Wt % | C7 |
|---|---|---|
| Sodium lauryl sulfate | 7.20 | 7.2 |
| Sodium soap (85/15 tallow/cocco) | | 24 |
| Sodium hydroxide | 2.34 | 2.34 |
| WATER SOLUBLE ORGANIC SOLVENTS | | |
| Sorbitol | 14.5 | 0.5 |
| Polyethylene Glycol (CARBOWAX 200) | 5.0 | 5 |
| Propylene glycol | 10.2 | 10.2 |
| Isopropyl alcohol | 1.23 | 1.23 |
| PARSOL MCX | 1.0 | 1.0 |
| Minors (e.g., color preservatives, etc) | 1.94 | 1.94 |
| Water | 26.2 | 17 |
| Wt bar composition per gm Fibrous network (SF3) | 100 | 100 |
| Vol % Fabricated Polymer Network (Non-woven SF3) | 90 | 90 |
| Water + water soluble organic solvent | 57.1 | 33.9 |

The fibrous network that may be used is the 100% polyethylene terephthalate non-woven, designated SF-3 (X-87) and used in Ex1.

The Exemplary and comparative articles would be prepared as described for Example 1.

The retention of the sunscreen, PARSOL MCX, on skin washed with the exemplary and comparative cleansing articles may be estimated using the In-vitro Skin Retention Test described in the EVALUATION METHODOLOGY section.

It is expected that approximately twice as much PARSOL MCX is retained on skin washed with the exemplary composition Ex 16 compared with skin washed with the comparative composition C7.

Example 17-20 and Comparative 8-14

Model perfume components having different hydrophobicities as measured by $\phi_{o/w}$ may be incorporated into the fibrous cleansing bars designated A and B in Table 8 at a total perfume level of 1.8%. Dilutions of these compositions may be evaluated for perfume intensity in the head space over the solution (equilibrated closed for 30 minutes) and over forearms washed under controlled conditions with the fibrous bars (see SPME Analysis of Fragrance Retention in EVALUATION METHODOLOGY section).

The evaluations may be made by an expert perfume panel (10 members) using a paired comparison methodology (randomized "1$^{st}$ composition evaluated"; forced choice, e.g., "which solution or which washed forearm has a more intense perfume smell". An experimental composition would be declared a "winner" in the attribute tested, i.e., produces a more intense perfume odor, when its preference score exceeds 60% (more than 6 out of 10 panelists).

The experimental results expected are summarized in Table 10. Compositions falling within the scope of the invention (water plus water soluble solvent level exceeding 40% AND partition coefficient>500) are expected to provide a high release of perfume relative to control compositions (comparatives) falling outside the scope.

TABLE 8

Compositions used in Examples 17-20 and Comparatives 8-14

| COMPONENT (as 100% active) | A Wt % | B |
|---|---|---|
| HYDROUS COMPOSITION | | |
| Stearic acid/palmitic acid blend | 14 | |
| Coconut fatty acid | 9 | 4 |
| 12 hydroxy stearic acid | 3.5 | |
| lauric acid | 3.06 | |
| sodium lauryl sulfate | 7.20 | |
| Sodium soap (85/15 tallow/cocco) | | 80.0 |
| Sodium hydroxide | 2.34 | |
| WATER SOLUBLE ORGANIC SOLVENTS | | |
| Sorbitol | 14.5 | |
| Polyethylene Glycol (CARBOWAX 200) | 5.0 | |
| Propylene glycol | 10.2 | |
| Isopropyl alcohol | 1.23 | |
| Glycerin | | 0.2 |
| MODEL PERFUME (see Table 9) | 1.8 | 1.8 |
| Minors (e.g., color preservatives, etc) | 1.94 | 0.5 |
| Water | 26.2 | 13.5 |
| Water + water soluble organic solvents | 57.1 | 13.5 |
| OVERALL FIBROUS BAR COMPOSITION | | |
| Wt Fibrous network (gm) | | |
| Wt Hydrous composition (gm) | | |
| Wt Hydrous composition per gm Fibrous network (SF3) | 100 | 100 |
| Vol % Fabricated Polymer Network (Non-woven SF3) | 90 | 90 |

TABLE 9

Lathering Composition of Example 2 and Comparatives 2 and 3

| | Model Perfume (1:1 mixture included at 1.8% level based on the hydrous composition) | φo/w | K | Hydrous Composition | % water + water-soluble organic solvent |
|---|---|---|---|---|---|
| C8 | Benzyl acetate/acetaldehyde | 81/167 | 0.32/0.008 | A | 57.1 |
| C9 | Benzyl acetate/acetaldehyde | 81/167 | 0.32/0.008 | B | 13.5 |
| C10 | Phenylethylalcohol/hydroxycitonellal | 22.9/34.7 | 0.1/0.05 | A | 57.1 |
| C11 | Phenylethylalcohol/hydroxycitonellal | 22.9/34.7 | 0.1/0.05 | B | 13.5 |
| Ex17 | Methyl ionone/lilial | 10,000/32,360 | 5.2/0.42 | A | 57.1 |
| C12 | Methyl ionone/lilial | 10,000/32,360 | 5.2/0.42 | B | 13.5 |
| Ex18 | Tetrahydrolinalylacetate/citronellyl acetate | 31,600/19,054 | 5.5/6 | A | 57.1 |
| C13 | Tetrahydrolinalylacetate/citronellyl acetate | 31,600/19,054 | 5.5/6 | B | 13.5 |
| Ex19 | Limonene/citronellene | 23,000/43,651 | 98/120 | A | 57.1 |
| C14 | Limonene/citronellene | 23000/43,651 | 98/120 | B | 13.5 |
| Ex20 | p-cymene/alpha-pinene | 31,000/29648 | 265/280 | A | 57.1 |
| C15 | p-cymene/alpha-pinene | 31,000/29648 | 265/280 | B | 13.5 |

TABLE 10

Perfume intensity evaluation results

| | Greatest Perfume Intensity Judged by Expert Panel | |
|---|---|---|
| Paired Comparison | Head Space (15% solution of experimental compositions) | Forearms after Wash with experimental compositions after 30 minutes |
| C8 VS C9 | No Difference | No Difference |
| C10 VS C11 | No Difference | No Difference |
| Ex 17 VS C12 | Ex 17 | Ex 17 |
| Ex 18 VS C13 | EX 18 | Ex 18 |
| Ex 19 VS C14 | Ex 19 | — |
| Ex 20 VS C15 | EX 20 | Ex 20 |

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A fibrous cleansing bar comprising:
   i) a fabricated polymer network having a porosity greater than about 0.95 selected from the group consisting of a 3 dimensional bat of a pleated woven or non-woven textile and reticulated polyurethane or modified polyurethane; and
   ii) a solid or semi-solid hydrous lathering composition in which is at least partially distributed the fabricated polymer network, said hydrous lathering composition comprising:
      a) a foaming surfactant;
      b) Type 2 perfumes having an octanol/water partition coefficient of at least about 500 and a volatility constant of less than about 20 atmospheres;
      c) water;
      d) optionally, a water soluble organic solvent;
   wherein the water plus the optional water soluble solvent comprises at least about 50% of the hydrous lathering composition by weight;
   wherein the fabricated polymer network is at least partially distributed in the solid or semi-solid lathering composition occupying at least about 75% of the volume of said lathering composition; and wherein the weight ratio of the hydrous lathering composition to the fabricated polymer network is in the range from about 30 to 1 to about 2000 to 1.

2. The fibrous cleansing bar according to claim 1 wherein the fabricated polymer network is a continuous network of bonded fibers.

3. The fibrous cleansing bar according to claim 2 wherein the fabricated polymer network is a web comprised of fibers selected from polyethylene terephthalate, polyethylene, polypropylene, polyamide, cellulose, modified or regenerated cellulose, and blends thereof.

4. The fibrous cleansing bar according to claim 1 wherein the fabricated polymer network comprises a plurality of nonbonded fibers wherein said fibers have a length to diameter ratio of from about 50 to 1 to about 100,000 to 1.

5. The fibrous cleansing bar according to claim 1 wherein the fabricated polymer network comprises an open cell reticulated polyurethane or modified polyurethane foam.

6. The cleansing composition according to claim 1 wherein at least 25% by weight of the foaming surfactant is an anionic surfactant selected from the group consisting of $C_{10}$ to $C_{18}$ alkyl carboxylates, $C_{10}$ to $C_{18}$ alkyl sulfates, $C_{10}$ to $C_{18}$ alkyl ethoxy sulfates, $C_{10}$ to $C_{18}$ acyl isethionates, and mixtures thereof.

7. The fibrous cleansing bar according to claim 1 further comprising a Type 3 perfume having a volatility constant of at least about 20 atmospheres.

8. The fibrous cleansing bar according to claim 7 wherein the Type 3 perfume comprises molecules selected from the group consisting of allo-ocimene, allyl caproate, allyl heptoate, anisole, camphene, carvacrol, carvone, citral, citronellal, citronellol, citronellyl nitrile, coumarin, cyclohexyl ethylacetate, p-cymene, decanal, dihydromyrcenol, dihydromyrcenyl acetate, dimethyl octanol, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, naphthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, and verdox.

9. The fibrous cleansing bar according to claim 1 wherein the Type 2 perfume comprises molecules selected from the group consisting of allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl acetate, citronellyl isobutyrate, citronellyl propionate, cuminic aldehyde, cyclohexylsalicylate, cyclamen aldehyde, cyclomyral, dihydro isojasmonate, diphenyl methane, diphenyl oxide, dodecanal, dodecalactone, ethylene brassylate, ethylmethyl phenylglycidate, ethyl undecylenate, exaltolide Galoxilide® (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, γ-ionone, α-irone, isobutyl benzoate, isobutyl quinoline, Iso E Super® (7-acetyl,1,2,3,4,5,6,7,8-octahydro,1,1,6,7-tetramethyl napthalene), cis-jasmone, lilial, linalyl benzoate, 20 methoxy naphthaline, methyl cinnamate, methyl eugenol, methylionone, methyl linoleate, methyl linolenate, musk indanone, musk ketone, musk tibetine, myristicin, neryl acetate, δ-nonalactone, γ-nonalactone, patchouli alcohol, phantolide, phenylethyl benzoate, phenylethylphenylacetate, phenyl heptanol, phenyl hexanol, α-santalol thibetolide, tonalid, δ-undecalactone, γ-undecalactone, vertenex, vetiveryl acetate, yara-yara and ylangene.

10. The fibrous cleansing bar according to claim 1 wherein the water soluble organic solvent is selected from the group consisting of a C1 to C3 alcohols, monoethanolamine, triethanolamine, glycerol, propylene glycol, sorbitol, sucrose, polyethylene glycol and mixtures thereof.

11. The fibrous cleansing bar according to claim 1 wherein the level of water plus optional water soluble organic solvent comprises at least about 60% of the hydrous composition by weight.

12. The cleansing article according to claim 1 wherein the fabricated polymer network occupies at least about 90% of the volume of the lathering composition.

* * * * *

UNITED STATES PATENT AND TRADEMARK OFFICE
CERTIFICATE OF CORRECTION

PATENT NO. : 7,348,299 B2  
APPLICATION NO. : 11/152600  
DATED : March 25, 2008  
INVENTOR(S) : Diane Marie Keenan et al.

Page 1 of 1

It is certified that error appears in the above-identified patent and that said Letters Patent is hereby corrected as shown below:

On the Title page, item [75]:  
The inventors list should be corrected to read:

Diane Marie Keenan, Derby, CT

Andre Marie Puleo, Stratford, CT

Melissa Ann Cline, East Hardford, CT

David Robert Williams, Monroe, CT

Liam Anthony Murray, Monroe, CT

On the Title page, item [73]:  
The Assignee should be corrected to read:

-- Conopco, Inc. d/b/a Unilever, Englewood Cliffs, NJ --

Signed and Sealed this

Twenty-fourth Day of June, 2008

JON W. DUDAS  
*Director of the United States Patent and Trademark Office*